US00PP09803P

United States Patent [19]

Stemkens

[11] Patent Number: Plant 9,803

[45] Date of Patent: Feb. 11, 1997

[54] GERANIUM PLANT NAMED 'SANRED'

[75] Inventor: Henricus G. W. Stemkens, Hoorn, Netherlands

[73] Assignee: S&G Seeds B.V., Enkhuizen, Netherlands

[21] Appl. No.: 572,832

[22] Filed: Dec. 14, 1995

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Lynn Marcus-Wyner

[57] ABSTRACT

A new Ivy-leaved geranium particularly distinguished by its well-branched shape and compact growth, early appearing light red purple single flowers which do not set seed with good precocity and floral richness.

1 Drawing Sheet

BACKGROUND OF THE NEW PLANT

The present invention comprises a new distinct cultivar of ivy-leaved geranium, botanically known as *Pelargonium peltatum* hybrid. The new cultivar is propagated from cuttings from the cross of L40 and N299. L40 is a light red purple flowering peltatum having no pollen L40 is not commercially available and is not known by any synonyms. N299 is a red colored peltatum, with vigorous growth and having pollen. N299 is not commercially available and is not known by any synonyms. Neither L40 or N299 have been patented. As a result of this cross the present cultivar was created in 1991 in Enkhuizen, Netherlands and has been repeatedly asexually reproduced by cuttings in Enkhuizen, Netherlands and Stuttgart, Germany over a three year period. It has been found to retain its distinctive characteristics through successive propagations, and this novelty appears to be firmly fixed.

DESCRIPTION OF THE DRAWING

The new geranium plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics were collected from asexual reproductions carried out in Enkhuizen, Netherlands. The plant history was taken on 12 week old plants, blossomed under natural light in a greenhouse. Color readings were taken in the greenhouse under ambient light. Color references are primarily to R.H.S. Colour Chart of The Royal Horticultural Society of London.

The Plant

Classification

*Botanical.*—*Pelargonium peltatum*—Hybrid.

*Commercial.*—Ivy-leaved geranium.

Parentage

*Female parent.*—A seedling named L40 is one of our seedlings from our L-generation of plants bred in 1986.

*Pollen parent.*—A seedling named N299 is one of our seedlings from N-generation of plants bred in 1987.

Form: Very compact, hanging.

Shape: Round.

Stalk length: About 170–220 mm in April and 430–490 mm in September.

Number of stems per stalk: Approximately 6–8 from May until the end of September.

Number of stalks per plant: Approximately 7–9 in October.

Intermode length: About 38–75 mm depending on the light where the plant is propagated.

Growth rate: Hanging and vigorous.

Strength: Very good.

Branching character: Very good branching.

Foliage:

*Quantity.*—Many robust leaves.

*Size.*—Small, from 42–55 mm.

*Shape.*—5 lobed, peltate.

*Texture.*—Hairy at young leaf stage (1 cm long), becoming smoother with increased maturity.

*Zonation.*—Almost circular, diameter 2–4 mm, dark brown.

Ribs and veins: 7 Ribs.

Color:

*Upper side.*—Medium green 141B.

*Lower side.*—Light green 141C.

Length of leaf stem: 35–45 mm.

The Bud

Peduncle length: 110–130 mm, depending on the season.

Size:

*Diameter.*—2–3 mm.

*Length.*—12 mm.

Shape: Elliptical.

Form: Ovoid and pointed.

Rate of opening: Medium.

Color:

*When sepals first divide.*—141C.

*When petals begin to unfurl.*—141D.

Sepals:

*Color.*—Inside—141D. Outside—141D.

*Form.*—Curling back.

Pedicel of florets:

*Length.*—About 18–22 mm.

*Strength.*—Very strong, the florets are arranged asymmetric round the middle of the cluster. The florets are approximately 30 mm in diameter.

*Color.*—One side 141C, one side 183C.

The Flower

Blooming habit: Continuous and profusely from April until October.

Size: Approximately 60–70 mm.
Borne: In a cluster having between 6–8 flowers per cluster.
Form: Horizontal symmetric, quite open. When the flowers mature, the petals curl back.
Petals:
*Numbers.*—5 per floret, between 100–120 clusters in one season per plant.
*Arrangement.*—2 upper petals, broader. 3 lower petals, smaller.
*Form.*—Obcordate—upper.
*Color.*—Outer petal—57A, red purple. Inside petal—pink (lower) or pink with stripes (upper).
*Markings.*—See pattern.
*Reverse side.*—Pink 62B with red purple.
*Pattern.*—The upper two petals have two long red purple margins (like lines) (colour 59C) which fade into the veins. Between the two lines the colour is pink (62B). The reverse side has the same stripes, but lighter in colour. The lower petals sometimes have very small (2 mm) pink lines, mostly 2. The outer parts of the petals are red purple colored (63A).
*Texture.*—Smooth.
*Appearance.*—Satiny.
Petals remain on stem about 5–7 depending on the weather.
Persistence: Petals drop, so no picking of matured clusters.
Disease resistance: Sanred does not suffer from Botrytis.
Weather resistance: Sanred is not unusually affected by wet or hot weather.
Lasting quality:
*On the living plant in pot.*—About 10–14 days.
*As a cut flower.*—About 5 days.
Fragrance: No perceptible fragrance.

Reproductive Organs

Stamens:
*Anthers.*—Totally shriveled, and yellow in color.
*Filaments.*—Usually 7, about 1 mm in length, and white in color.
Pollen: None.
Pistils:
*Number.*—One.
*Length.*—Approximately 4 mm.
*Stigmas.*—Pink in color, divided in 5 papillae.
Ovaries: Green in color.
Seed: Non fertile.

What is claimed is:

1. A new and distinct cultivar of ivy-leaved geranium plant substantially as herein shown and described, particularly distinguished by its very short internodes and well branched plant, and its early appearing light red purple single flowers which do not set seed.

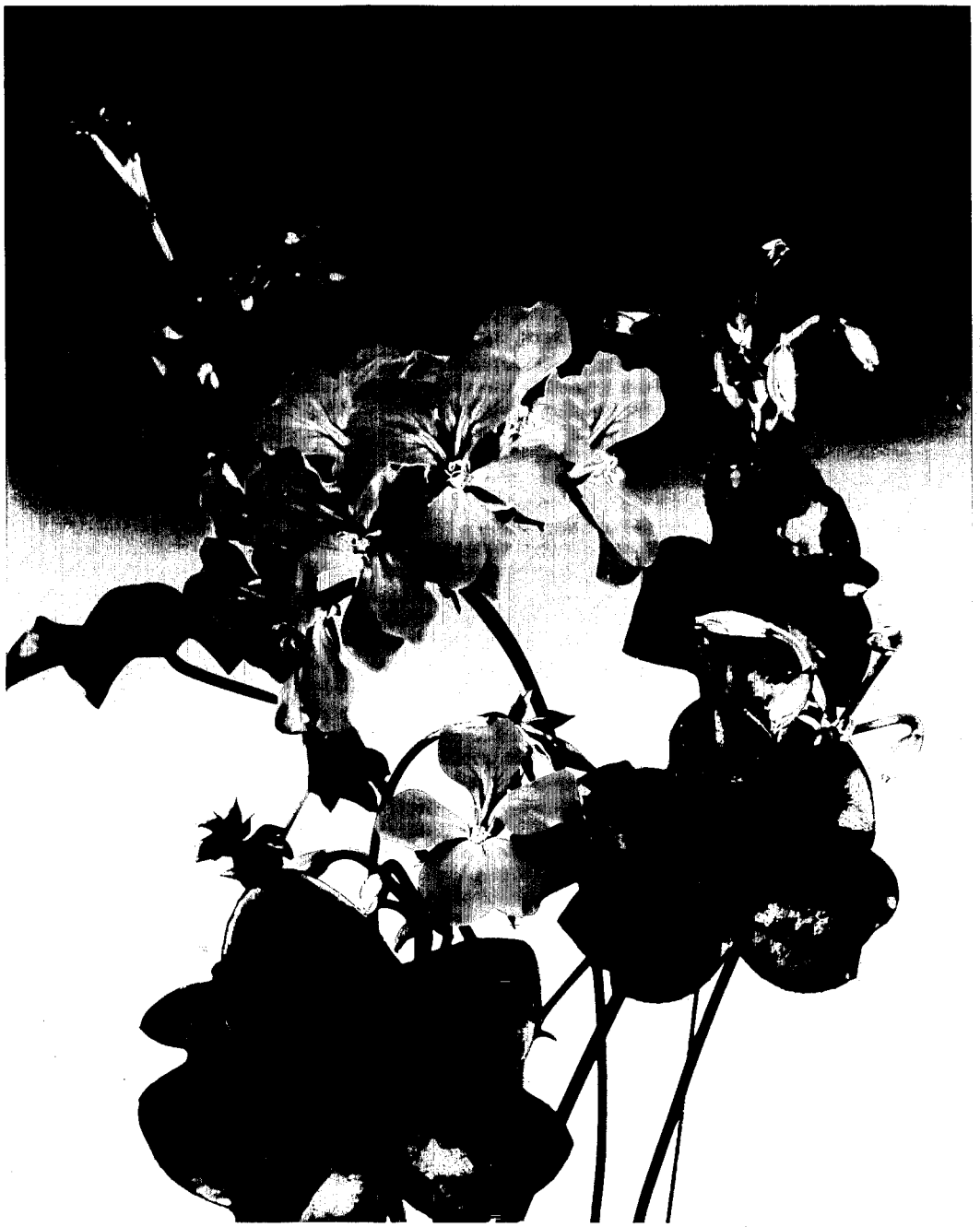

* * * * *